(12) United States Patent
Cerrina et al.

(10) Patent No.: US 7,179,568 B2
(45) Date of Patent: Feb. 20, 2007

(54) DEFECT INSPECTION OF EXTREME ULTRAVIOLET LITHOGRAPHY MASKS AND THE LIKE

(75) Inventors: Francesco Cerrina, Madison, WI (US); Adam Pawloski, San Jose, CA (US); Lin Wang, Baton Rouge, LA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 77 days.

(21) Appl. No.: 10/616,863

(22) Filed: Jul. 10, 2003

(65) Prior Publication Data

US 2005/0008944 A1    Jan. 13, 2005

(51) Int. Cl.
*G03F 9/00*    (2006.01)

(52) U.S. Cl. .............................. 430/5; 430/30; 430/296; 430/942; 430/966; 430/967; 382/144

(58) Field of Classification Search .................... 430/5, 430/30, 296, 942, 966, 967; 382/144
See application file for complete search history.

(56) References Cited

U.S. PATENT DOCUMENTS

| | | | |
|---|---|---|---|
| 5,763,123 A | | 6/1998 | Shishido et al. |
| 5,935,737 A | * | 8/1999 | Yan ................... 430/5 |
| 6,002,740 A | | 12/1999 | Cerrina et al. |
| 6,091,488 A | | 7/2000 | Bishop |
| 6,335,531 B1 | | 1/2002 | Somerville et al. |
| 2002/0088952 A1 | | 7/2002 | Rao et al. |

FOREIGN PATENT DOCUMENTS

| EP | 0922996 A1 | 6/1999 |
|---|---|---|
| JP | 63056649 | 3/1988 |
| KR | 2003-0030280 | 4/2003 |

OTHER PUBLICATIONS

K.B. Nguyen et al., Optical Society of America, At-wavelength inspection of EUVL mask defects with a 1X Offner ring-field system, OSA TOPS on Extreme Ultraviolet Lithography, vol. 4, pp. 49-53, May 1996, Washington, D.C.

S.J. Spector et al., American Vacuum Society, Technique for rapid at-wavelength inspection of extreme ultraviolet mask blanks, J. Vac. Sci. Technol., vol. 17, No. 6, pp. 3003-3008, Nov./Dec. 1999, New York, New York.

* cited by examiner

*Primary Examiner*—Christopher G. Young
(74) *Attorney, Agent, or Firm*—Reinhart Boerner Van Deuren s.c.

(57) ABSTRACT

A dark-field imaging method for detecting defects in reflective lithography masks (e.g., extreme ultraviolet (EUV) masks) used, e.g., in processes for the fabrication of microelectronic devices. A mask blank is coated with a photoresist layer having a fluorescent dye incorporated therein. The photoresist layer is exposed to a source of radiation (e.g., EUV radiation or glancing soft X-rays). In areas of the mask blank having defects the combined direct and reflected radiation will be insufficient fully to expose the photoresist layer. After development, photoresist will remain on the mask blank surface in areas corresponding to defects. Illumination with the excitation wavelength of the fluorescent dye reveals the location of any remaining photoresist, which can be detected using an optical microscope, thereby to detect defects in the mask blank.

21 Claims, 4 Drawing Sheets

DEFECT INSPECTION OF EXTREME ULTRAVIOLET LITHOGRAPHY MASKS AND THE LIKE

FIELD OF THE INVENTION

This invention pertains generally to masks used in lithography processes for the fabrication of microelectronic devices and micromechanical structures, and more particularly to masks used in extreme ultraviolet (EUV) lithography and methods and devices for inspecting such masks to determine if there are defects therein.

BACKGROUND OF THE INVENTION

Lithography is at the heart of processes for the fabrication of microelectronic devices, such as integrated circuits, and micromechanical structures. The basic process of producing a microelectronic device involves the modification of the surface material of a semiconductor substrate, such as of silicon, in a pattern. The interplay of the material changes and the pattern defines the electrical characteristics of the microelectronic device. A similar process can be used to form micromechanical devices, by, for example, electroplating metal structures in a desired pattern onto a substrate. Lithography is used to define the pattern on the substrate which will be doped, etched, or otherwise modified to form the microelectrical or micromechanical device.

In a basic lithography process for the fabrication of microelectronic or micromechanical devices, a photo sensitive material, such as polymethylmethacrylate (PMMA), is deposited on a substrate surface. The photoresist is sensitive to radiation, e.g., X-rays or extreme ultraviolet (EUV) radiation, and, depending on the photoresist used, portions of the photoresist that are exposed to the radiation may be removed (or left remaining) by a development process. The microelectronic or micromechanical device is formed by etching or otherwise modifying the substrate in the areas from which the photoresist has been removed. To form a desired pattern in the photoresist, the radiation that is used to expose the photoresist is passed through or reflected off of a lithography mask that defines the pattern that is to be transferred to the photoresist.

An exemplary portion of an EUV lithography mask 10, which may be used in a microelectronic device fabrication process, is illustrated schematically in FIG. 1. The EUV mask 10 is formed on an EUV mask blank 12 which includes an EUV reflective substrate 14 upon which are deposited multiple layers of material forming an interference stack 16 which enhances the overall EUV reflectivity of the mask 10. In general, the EUV reflectivity of the mask blank 12 will be greater than 70%. A pattern is formed on the mask 10 by forming a layer of non-reflective material 18 on the mask surface, i.e., on the surface of the interference stack 16. The non-reflective material 18 is patterned in a highly accurate manner, e.g., using an electron beam lithography system, to produce a pattern of the non-reflective material 18 on the EUV mask 10 which will define the pattern of the microelectronic or micromechanical structure to be fabricated using the mask 10.

For device fabrication using an EUV mask 12, a photoresist layer deposited on a target substrate wafer to be patterned is positioned to receive EUV radiation that is reflected off of the EUV mask 10. EUV radiation 20, from an EUV source, is directed at the patterned surface of the EUV mask 10. (It is noted that multilayer EUV masks of the type described herein typically are designed for operation at normal incidence of the EUV radiation 20 thereon. A large incidence angle for the EUV radiation 20 is shown in FIG. 1 for ease of illustration.) In areas of the mask surface upon which the patterned EUV non-reflective material 18 remains the impinging EUV rays 20 are absorbed. Hence, there is no reflection of EUV radiation from these areas onto the target substrate. In areas of the EUV mask surface on which there is no remaining non-reflective material 18 the incident EUV rays 20 are reflected 22 and directed to the photoresist covered surface of the target substrate wafer. In this manner, after a development process, the pattern of EUV non-reflective material 18 formed on the surface of the EUV mask 10 is transferred to the target substrate. Up to 20–25 or more masks may be employed for the fabrication of a single integrated circuit chip.

To ensure accurate reproduction of the mask pattern on the target substrate wafer, it is essential both that the pattern of non-reflective material 18 formed on the EUV mask 10 be accurately produced and defect free and that the mask blank 12 on which the EUV mask 10 is formed be defect free. Defects in the mask blank 12, particularly within the interference stack 16, may distort or reduce the intensity of the EUV rays 22 reflected from the mask 10, resulting in a corresponding defect in the pattern formed on the target substrate wafer. Defects as small as 5–10 nm can severely disrupt image formation in EUV lithography for the production of, for example, semiconductor microelectronic circuitry. It is very important, therefore, that any defects in the mask blank 12 be detected, preferably before the mask is patterned for use in fabrication and the resulting error is detected in the end product which the mask is used to fabricate. It also is particularly important that such defects in the mask blank 12 be detected early on, in that, using current technologies, EUV masks can cost $100,000 or more to produce.

Generally, two types of defects in the interference stack 16 of an EUV mask blank 12 typically are encountered, one type may be relatively easy to detect, the other type is much more difficult to detect. The first type of defect is illustrated in FIG. 2. In this case, a defect 24 in the interference stack 16 of the mask blank 12 results in a physical manifestation 26 on the surface of the mask blank 12. This distortion 26 near the surface of the mask blank 12, although small, can adversely affect the reflection of EUV rays from a mask that is made from the mask blank 12, thereby ruining the mask. However, since the defect 24 is manifest as a physical distortion 26 at the surface of the mask blank 12, such a defect may be relatively easy to detect.

A more difficult to detect type of defect that may occur in an EUV mask blank 12 is illustrated in FIG. 3. In this case, the defect 28 is buried in the multilayer interference stack 16. The defect 28 results in a distortion 30 in the layers of the interference stack 16. This distortion will adversely affect the reflection of EUV rays by the interference stack 16, by unpredictably shifting the phase of EUV rays passing through the stack, thereby ruining any mask made from a mask blank having such a defect. In this case, the defect 28 does not manifest itself at the surface of the interference stack 16. Thus, although a defect 28 which can destroy the effectiveness of an EUV mask made from the mask blank 12 is present, the surface of the mask blank may remain perfectly smooth, and may thus appear to be defect free. Such an imbedded defect 28 is, therefore, very difficult to detect. Currently, such a defect 28 could be detected by examining the entire mask blank 12 for defects using a device such as an X-ray microscope, which employs a very narrow penetrating beam to examine the interference stack.

However, since defects on the order of 10 nm can ruin the mask blank 12, and a typical mask blank may be four inches by four inches in size, the time required to examine the entire mask blank for such defects using the small field of view provided by an X-ray microscope or similar device makes this method of mask inspection very time consuming, expensive, and, therefore, relatively impractical. At-wavelength inspection of EUV masks also is extremely costly, because of the scarcity of EUV sources.

What is desired, therefore, is a new method for the inspection of EUV lithography masks, and the like, for the detection of defects therein, including defects that are not physically manifested at the surface of the mask blank. The preferred method should be both sensitive, i.e., have the ability to detect very small defects, and accurate, i.e., have the ability to reject background signals. Furthermore, such an inspection method should be able to employ radiation sources other than EUV sources, which may be more readily available.

SUMMARY OF THE INVENTION

The present invention provides a method for defect inspection of extreme ultraviolet (EUV) lithography masks and the like. A method in accordance with the present invention may be used to find defects in EUV mask blanks with both high sensitivity, i.e., the ability to detect very small defects, and accuracy, i.e., the ability to reject background signals. An EUV mask defect inspection method in accordance with the present invention employs a "dark field" imaging technique. By such a dark field method, only defects appear in the field of view of the inspection system. In other words, by this method a signal only appears if, and where, a defect is found on the mask blank being inspected.

In accordance with the present invention, a multi-layer EUV mask blank, or other structure to be inspected for defects, is coated with a layer of photoresist (e.g., PMMA or UV-6). The blank is then exposed to a source of EUV radiation or X-rays matching the Bragg condition for a time sufficient to fully expose for development the photoresist applied over areas of the mask blank that are free of defects. The photoresist layer is exposed with a sufficient intensity and duration to fully expose the photoresist layer for complete development and removal if there were no defects present in the mask blank. The amount of radiation seen by the photoresist layer is the sum of the incoming radiation beams and the beams reflected from the mask surface. If the mask blank is perfect, after development no photoresist will be left on the mask blank surface. If, however, the blank has defects, the area immediately above and surrounding a defect on the mask blank surface will receive less exposure by reflection, because the reflected beam will be missing or distorted, and thus the photoresist in the area corresponding to a defect will not receive a sufficient dose of radiation to be fully developed. The defect location may thus easily be determined by photoresist remaining on the mask blank surface after development. In accordance with the present invention, the photoresist preferably is loaded with a fluorescent dye. After development, illumination with the excitation wavelength of the dye will quickly and effectively reveal the location of any remaining resist. An optical microscope, such as a conventional confocal microscope, is sufficient to detect a fluorescent area on the surface of the mask blank, and, therefore, the presence of a defect therein.

Since the present invention employs a dark-field type of imaging (only the presence of defects will induce fluorescence) it is extremely effective and efficient. A method for mask defect inspection in accordance with the present invention also is very sensitive. Very small defects, on the order of 10 nm, or less, and even if deeply imbedded in the interference stack of an EUV mask blank, can be detected in this manner. Mask defect inspection in accordance with the present invention also is both economical and convenient. In accordance with the present invention an EUV mask blank can be inspected for defects using other than at-wavelength radiation, e.g., using an X-ray source that can readily be purchased commercially.

Further objects, features, and advantages of the invention will be apparent from the following detailed description taken in conjunction with the accompanying drawings.

DETAILED DESCRIPTION OF THE INVENTION

Figure 1:
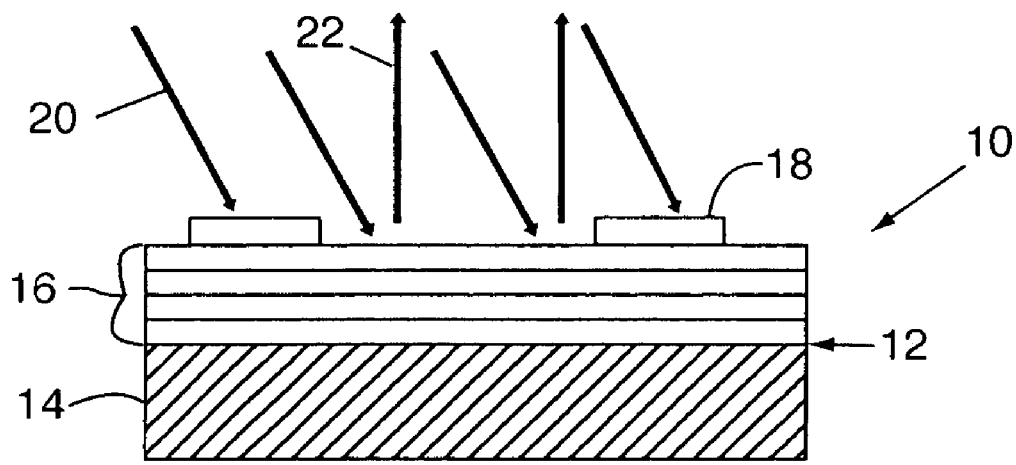
FIG. 1 is a schematic cross-sectional illustration of an exemplary portion of an extreme ultraviolet (EUV) lithography mask being exposed to radiation during use thereof.
Figure 2:
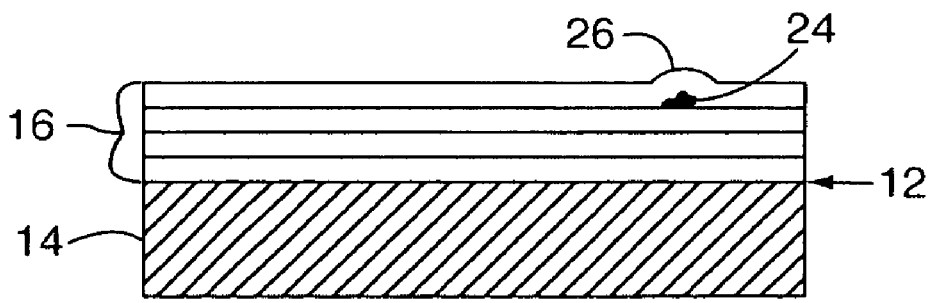
FIG. 2 is a schematic cross-sectional illustration of an exemplary portion of an EUV lithography mask blank having a defect therein resulting in a physical manifestation on the surface of the mask blank.
Figure 3:
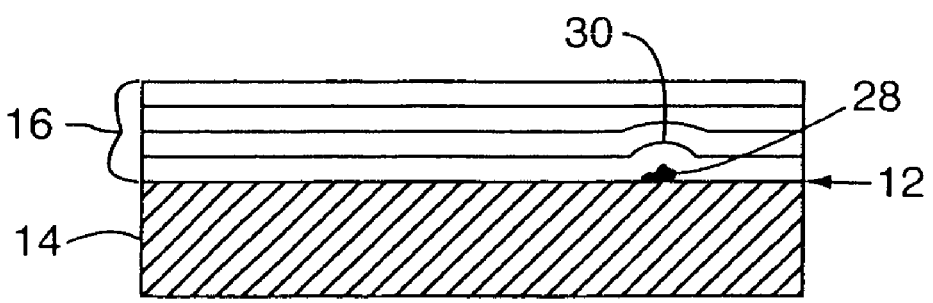
FIG. 3 is a schematic cross-sectional illustration of an exemplary portion of an EUV lithography mask blank having a defect therein that does not result in a physical manifestation on the surface of the mask blank.
Figure 4:
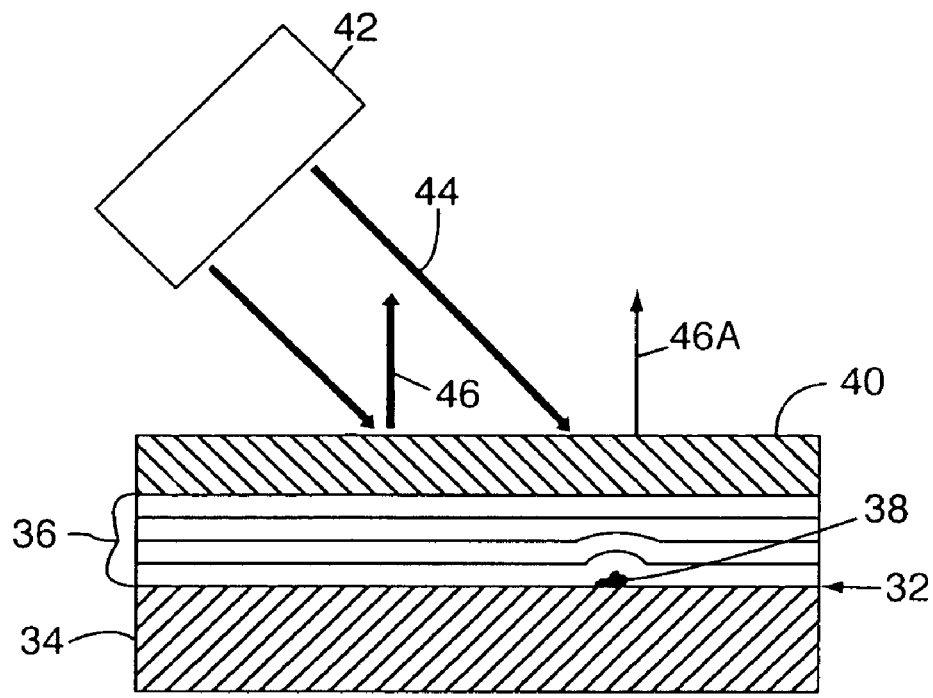
FIG. 4 is a schematic cross-sectional illustration of the exemplary portion of the EUV lithography mask blank of FIG. 3 having a photoresist layer applied thereto and being exposed to radiation from a radiation source in accordance with a method for detecting defects in the mask blank in accordance with the present invention.

A method for the detection of defects in extreme ultraviolet (EUV) lithography masks and the like in accordance with the present invention now will be described in detail beginning with reference to FIG. 4. FIG. 4 is a schematic cross-sectional illustration of a lithography mask blank 32 (e.g., an EUV lithography mask blank) to be inspected for defects in accordance with the present invention. As discussed above, the EUV mask blank 32 may include a reflective substrate 34 upon which is formed an interference stack 36, which enhances the reflectivity of the mask blank 32. One or more defects 38 may, or may not, be present in the mask blank. As is discussed above, a defect 38 in the mask blank, e.g., on or near the surface of the substrate 34 or in the interference stack 36, may destroy the effectiveness of a lithography mask formed from the mask blank 32. Specifically, the defect 38 in the mask blank will cause a phase shift in the EUV or other radiation reflected from the mask blank 32, thereby distorting, reducing, or eliminating the reflection from the mask in and around the area of the defect 38. It is an object of the present invention to detect such defects 38 in the mask blank with a high degree of both sensitivity and accuracy before the mask blank 32 is formed into a lithography mask.

In accordance with the present invention, the mask blank 32 to be inspected is coated with a photoresist layer 40. The photoresist layer 40 may be formed of a conventional photoresist material, such as polymethylmethacrylate (PMMA) or UV-6 UV-sensitive photoresist material. The photoresist material is applied over the interference stack 36 surface of the mask blank 32 and hardened in a conventional manner.

Preferably, a fluorescent dye material is incorporated in the photoresist layer 40. Exemplary fluorescent dye materials that may be incorporated in the photoresist layer 40 include Azure B, Cresyl Violet perchlorate, Rhodamine B, and Rhodamine 6 G. Of course, it should be understood that other fluorescent dye materials may be employed for this purpose in accordance with the present invention. The fluorescent dye material may be mixed in with the photoresist material before the photoresist material is applied to and hardened on the mask blank 32. Any such fluorescent dye material incorporated in the photoresist layer 40 preferably should not affect adversely normal exposure and development of the photoresist layer 40.

Figure 5:
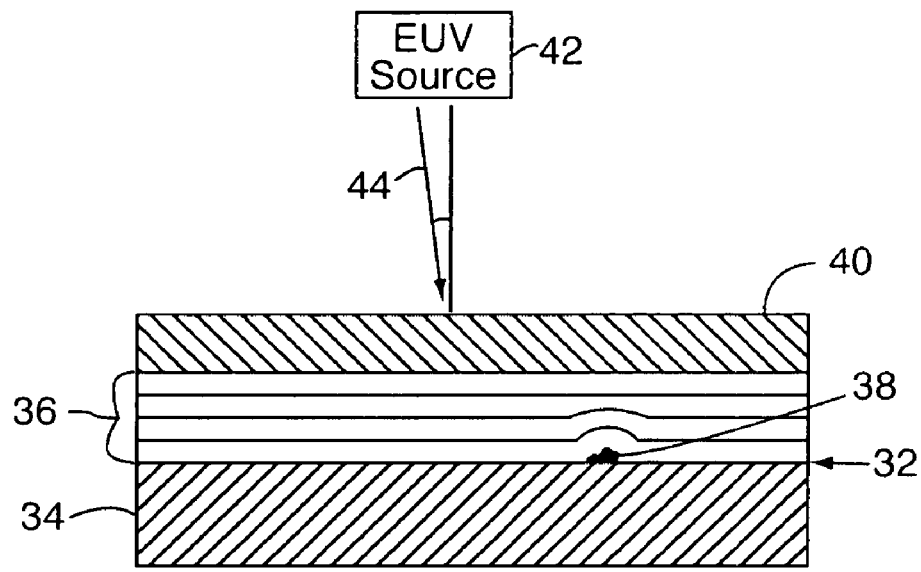
FIG. 5 is a schematic cross-sectional illustration of the exemplary portion of the EUV lithography mask blank of FIG. 4 being exposed to radiation from an EUV radiation source in accordance with a method for detecting defects in the mask blank in accordance with the present invention.
Figure 6:
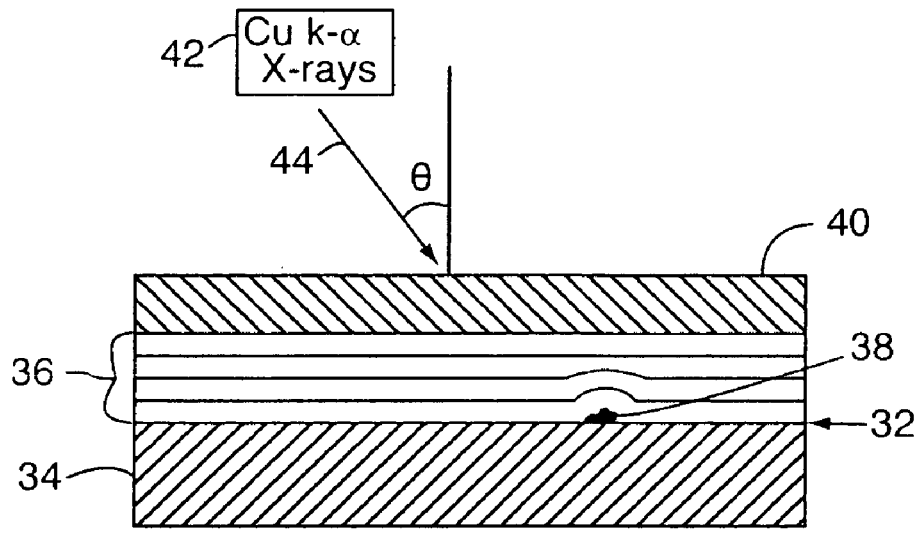
FIG. 6 is a schematic cross-sectional illustration of the exemplary portion of the EUV lithography mask blank of FIG. 4 being exposed to radiation from an X-ray radiation source in accordance with a method for detecting defects in the mask blank in accordance with the present invention.

After having applied and hardened the photoresist layer 40, in a conventional manner, the surface of the photoresist layer 40 is exposed using a radiation source 42. For example, a conventional EUV source 42 may be used to direct EUV radiation 44 at the surface of the photoresist layer 40. (As illustrated in FIG. 5, EUV radiation 44 is directed at near normal incidence to the surface of the photoresist layer 40.) However, EUV sources generally are scarce. In accordance with the present invention, a more conventional radiation source, e.g., an X-ray source, such as a Cu K-alpha X-ray source, may be used to direct X-rays 44 at the photoresist surface layer 40. Such an X-ray source can be purchased commercially, and outfitted with the appropriate collimating optics, to direct collimated X-rays 44 at the photoresist surface layer 40. Commercially available X-ray sources of this type are available from manufacturers such as Hamamatsu Corporation, Philips, and General Electric. Any other X-ray source, e.g., a synchrotron X-ray source, may be used to direct collimated X-ray radiation 44 at the photoresist layer 40. Whereas multilayered EUV mask blanks are designed for operation at normal incidence in the wavelength region around 13 nm (commonly referred to as EUV), for mask defect inspection in accordance with the present invention, a shorter wavelength (e.g., Cu K-alpha X-rays at 1.3 nm) and large incidence angles (e.g., around 84 degrees) may be used, as illustrated schematically in FIG. 6. Whatever radiation source is used, radiation exposure of the photoresist layer 40 should be uniform over the area of exposure.

The amount of radiation received by the photoresist layer 40 is given by the sum of the incoming 44 and reflected 46 radiation that passes through the photoresist layer 40 as the radiation is directed toward the interference stack 36 and reflected therefrom, respectively. It is noted that in an area of the mask blank 32 that includes a defect 38, the reflected radiation 46A is attenuated or completely missing. Thus, areas of the photoresist layer 40 located over such a defect 38 will receive less radiation exposure than defect free areas of the mask blank 32.

Figure 7:
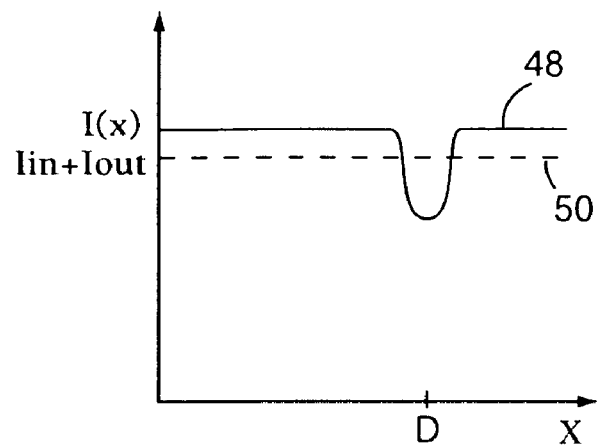
FIG. 7 is a graph illustrating schematically the combined incident and reflected radiation dose received by a photoresist layer applied to an EUV lithography mask blank in defect free and defect containing areas of the mask blank in a method for detecting defects in the mask blank in accordance with the present invention.

In accordance with the present invention, the photoresist layer 40 is exposed by the source 42 of (EUV or X-ray) radiation with radiation of a sufficient intensity and for a time sufficient to match the Bragg condition to fully expose for development the photoresist layer 40 in areas of the mask blank 32 in which there are no defects, i.e., in areas where there is full reflection from the interference stack 36. FIG. 7 is a simple graph illustrating the combined amount of radiation exposure ($I_{IN}+I_{OUT}$) 48 experienced by a photoresist layer across a mask blank 32 under inspection in accordance with the present invention. Line 50 indicates the exposure required for the photoresist layer 40 such that when the photoresist layer 40 is developed all of the photoresist material will be removed from the mask blank 32. As illustrated, the radiation exposure is selected such that the exposure 48 provided by the combined incoming (direct) and reflected beams exceeds this photoresist exposure threshold 50. In an area of the photoresist layer 40 corresponding to a position (x=D) in the mask blank 32 in which there is a defect, the combined exposure 48 provided by the incoming and reflected radiation beams is below the photoresist full exposure threshold 50. It should be understood that the exact radiation exposure intensity and exposure time required to achieve the desired condition illustrated will depend upon the radiation type and source employed as well as the photoresist layer material and thickness thereof. These variables may be adjusted to optimize the process for a desirable parameter such as reduced exposure time, reduced development time, increased accuracy, etc.

Figure 8:
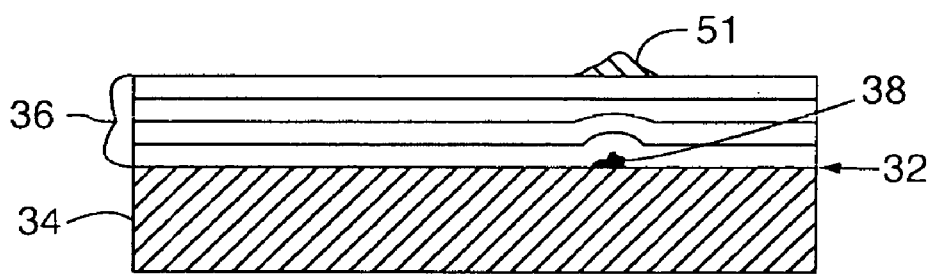
FIG. 8 is a schematic cross-sectional illustration of the exemplary portion of the EUV lithography mask blank of FIG. 4 after the photoresist layer has been developed.

After exposure of the photoresist layer 40 in the manner just described, the photoresist layer 40 is developed, in a conventional manner. In areas of the mask blank 32 where there are no defects, the entire photoresist layer 40 will be removed by the development process. However, as illustrated in FIG. 8, in areas of the mask blank 32 where defects 38 are present, a portion 51 of the photoresist layer, which, due to the presence of the defect 38, was not sufficiently exposed by the combined incoming and reflected radiation beams during exposure, will remain on the surface of the mask blank 32. The presence of any photoresist 51 on the surface of the mask blank 32 after development indicates the presence of a defect 38 in the mask blank 32.

A very small amount of photoresist 51 may remain on the surface of the mask blank 32 after development if a defect 38 is present therein. The presence of any remaining photoresist 51 may be determined using a scanning electron microscope (SEM), atomic force microscope (AFM), or a similar device. However, scanning the surface of the mask blank 32 using such a device to find any remaining photoresist 51 may be prohibitively time consuming. In accordance with the present invention, the photoresist 51 may be loaded with a fluorescent dye. Therefore, after development, illumination with the excitation wavelength of the dye will quickly and effectively reveal the location of any remaining photoresist 51. An optical microscope will be sufficient to detect the presence of a fluorescent area on the mask blank 32, thereby indicating the presence of a defect. Resolution is not an issue, since fluorescence can be used to detect optically single molecules. This dark-field type of imaging using scattered light is extremely effective and sensitive, since only the presence of defects, resulting in remaining photoresist 51 with a fluorescent dye therein, will induce fluorescence when exposed to illumination with the excitation wavelength.

Figure 9:
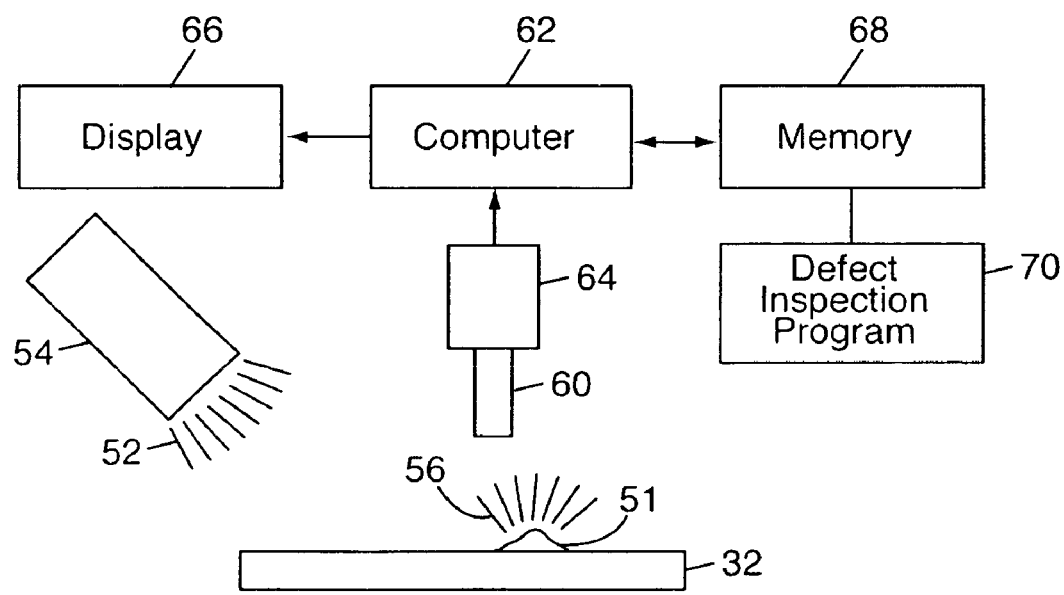
FIG. 9 is a schematic illustration of an exemplary system and method in accordance with the present invention for examining the exemplary portion of the EUV lithography mask blank of FIG. 6 to detect a defect therein.

An exemplary system for detecting remaining photoresist 51 on a mask blank 32 after development, to detect the presence of a defect therein, is illustrated schematically in FIG. 9. Light 52, containing the excitation wavelength of the fluorescent dye in the photoresist 51, if any, remaining on the mask blank 32, is directed toward the surface of the mask blank 32 from a conventional illumination source 54. The illuminating light 52 provided from the illumination source 54 excites the fluorescent dye material in the remaining photoresist material 51, inducing fluorescence 56. An optical microscope 60, such as, for example, a confocal microscope, is positioned to examine the illuminated surface of the mask blank 32. Any fluorescent area on the surface of the mask blank 32 is easily detected using such a microscope 60, thereby to detect the presence of a defect in the mask blank 32.

An operator may view an image of the illuminated mask blank 32 directly through the microscope 60, to detect manually the presence of a defect, if any, in the mask blank 32. Additionally, and/or alternatively, the process may be automated by coupling the microscope 60 used to examine the surface of the mask blank 32 to a computer system 62. For example, a video or other camera 64 may be coupled to the microscope 60 to provide a video or still image of the illuminated surface of the mask blank 32, as seen by the microscope 60, to the computer 62. (Appropriate conventional conversion of the analog video or still image signal provided by the camera 64 to a digital signal for use by the computer 62 is required.) The video or still image received by the computer 62 may be displayed in a conventional manner on a conventional computer display 66 coupled to the computer 62. The computer system 62 may include conventional memory 68 associated therewith, in which may be stored a defect inspection computer program 70 which may be run on the computer 62. The defect inspection program 70 may be used to analyze the digitized image of the illuminated surface of the mask blank 32 to detect automatically a fluorescent area on the surface of the mask blank 32, and, therefore, the presence of a defect in the mask blank 32. For example, the defect inspection program 70 may automatically and rapidly examine the picture elements (pixels) forming the image of the illuminated surface of the mask blank 32 to detect areas of the image having a pixel intensity which exceeds a certain threshold, indicating the presence of a fluorescent material on the illuminated surface of the mask blank 32. The result of the analysis performed by the defect inspection program 70 may be presented on the display 66 to an operator, indicating, e.g., the presence or absence of any detected fluorescent area on the surface of the mask blank 32 (and, therefore, the presence or absence of any defect in the mask blank 32). The defect inspection program 70 may also provide to the operator on the display 66 an indication of the location on the mask blank 32 of any detected defect, thereby facilitating repair of the mask blank, if possible.

An experiment was performed to prove the usefulness and effectiveness of defect inspection of EUV lithography masks in accordance with the present invention. In the experiment, the dye Rhodamine 6 G was added to a photoresist containing the polymer poly(methylmethacrylate) in a solvent of chlorobenzene. This dye exhibits fluorescence when stimulated with light at a wavelength near 528 nm, and the fluorescence was monitored in the range of wavelengths near 551 nm. The resist was spin coated onto substrates consisting of the multilayer stack with arrays of programmed defects to achieve a resist film thickness of approximately 100 nm. The sample was then exposed to EUV radiation at an energy of 92.5 eV (wavelength of 13.4 nm) using synchrotron radiation in several separate areas with incremental exposure doses. The exposed resist was then developed using a standard development process for poly(methylmethacrylate) resist, which employs of a mixture of methyl-isobutyl ketone and isopropyl alcohol solvents. In the exposed regions, the majority of the photoresist receives enough exposure dose to remove completely the film during development, however, in the regions above the programmed defects, the defects cause a phase mismatch between incident and reflected light from the substrate so that the total light intensity seen by the resist in these areas is less than in other areas of the film. The various exposed regions were scanned using a dark-field microscope capable of fluorescence imaging. The regions for which resist remained on the substrate were seen clearly in the optical microscope, and the patterns of the underlying programmed defects were identified clearly. To verify further that the locations of the remaining resist corresponded to the programmed defects, an atomic force microscope (AFM) was used to measure the height variations of the substrate across the areas where resist remained after development, to confirm that such regions corresponded exactly to the locations of the programmed defects.

It should be understood that the present invention is not limited to the particular exemplary applications and embodiments illustrated and described herein, but embraces all such modified forms thereof as come within the scope of the following claims. In particular, although described in detail herein with reference to an exemplary application to the detection of defects in EUV lithography mask blanks, it should be understood that the present invention also may be employed to detect defects in any similar reflective surfaces, objects and materials, wherein the determination of defect free reflection of radiation of any type therefrom is important.

What is claimed is:

1. A method for detecting defects in a lithography mask blank, comprising:
   (a) applying a photoresist layer directly onto a reflective surface of the mask blank;
   (b) exposing the photoresist layer with radiation having a wavelength and angle of incidence such that the photoresist layer is fully exposed by the combination of direct radiation and reflected radiation from the mask blank in areas of the mask blank in which there are no defects;
   (c) developing the exposed photoresist layer to remove the fully exposed photoresist from the mask blank; and
   (d) detecting photoresist remaining on the mask blank after development of the photoresist layer to detect defects in the mask blank.

2. The method of claim 1 wherein the photoresist layer includes a photoresist material selected from the group of photoresist materials consisting of PMMA and UV-6.

3. The method of claim 1 wherein the photoresist layer includes a fluorescent material incorporated therein.

4. The method of claim 3 wherein detecting the photoresist remaining on the mask blank after development includes illuminating the mask blank to excite the fluorescent material in the photoresist remaining on the mask blank after development of the photoresist layer.

5. The method of claim 4 wherein detecting the photoresist remaining on the mask blank includes detecting the excited fluorescent material using an optical microscope.

6. The method of claim 1 wherein the mask blank is an EUV mask blank.

7. The method of claim 1 wherein exposing the photoresist layer includes exposing the photoresist layer with an X-ray radiation source.

8. The method of claim 7 wherein exposing the photoresist layer includes exposing the photoresist layer with a Cu K-alpha X-ray source.

9. The method of claim 1 wherein exposing the photoresist layer includes exposing the photoresist layer with an EUV radiation source.

10. The method of claim 1 wherein detecting the photoresist remaining on the mask blank includes detecting the photoresist remaining on the mask blank using an atomic force microscope.

11. A method for detecting defects in an EUV lithography mask blank, comprising:
 (a) applying a photoresist layer including a fluorescent material incorporated therein to the EUV mask blank;
 (b) exposing the photoresist layer with radiation having a wavelength and angle of incidence such that the photoresist layer is fully exposed by the combination of direct and reflected radiation in areas of the mask blank in which there are no defects;
 (c) developing the exposed photoresist layer to remove the fully exposed photoresist from the EUV mask blank;
 (d) illuminating the mask blank to excite the fluorescent material in the photoresist remaining on the mask blank after development of the photoresist layer; and
 (e) detecting the illuminated photoresist remaining on the EUV mask blank after development of the photoresist layer to detect defects in the mask blank.

12. The method of claim 11 wherein the photoresist layer includes a photoresist material selected from the group of photoresist materials consisting of PMMA and UV-6.

13. The method of claim 11 wherein exposing the photoresist layer includes exposing the photoresist layer with an X-ray radiation source.

14. The method of claim 13 wherein exposing the photoresist layer includes exposing the photoresist layer with a Cu K-alpha X-ray source.

15. The method of claim 11 wherein detecting the photoresist remaining on the mask blank includes detecting the photoresist remaining on the mask blank using an optical microscope.

16. A method for detecting defects in a reflective material, comprising:
 (a) applying a photoresist layer directly onto a reflective surface of the reflective material;
 (b) exposing the photoresist layer with radiation having a wavelength and angle of incidence such that the photoresist layer is fully exposed by the combination of direct radiation and reflected radiation from the reflective surface in areas of the reflective material in which there are no defects;
 (c) developing the exposed photoresist layer to remove the fully exposed photoresist from the reflective material; and
 (d) detecting photoresist remaining on the reflective material after development of the photoresist layer to detect defects in the reflective material.

17. The method of claim 16 wherein the reflective material is an EUV lithography mask blank.

18. The method of claim 16 wherein detecting the photoresist remaining on the reflective material includes detecting the photoresist remaining on the reflective material using an atomic force microscope.

19. The method of claim 16 wherein detecting the photoresist remaining on the reflective material includes detecting the photoresist remaining on the reflective material using scattered light.

20. The method of claim 16 wherein the photoresist layer includes a fluorescent material incorporated therein.

21. The method of claim 20 wherein detecting the photoresist remaining on the reflective material after development includes illuminating the reflective material to excite the fluorescent material in the photoresist remaining on the mask blank after development of the photoresist layer.

* * * * *